United States Patent [19]

Vlattas

[11] Patent Number: 4,460,508
[45] Date of Patent: Jul. 17, 1984

[54] 5-DIAZACYCLOALKYLIMIDAZO[1,2-C][1,3]BENZODIAZEPINES

[75] Inventor: Isidoros Vlattas, Summit, N.J.

[73] Assignee: Ciba-Geigy Corporation, Ardsley, N.Y.

[21] Appl. No.: 417,747

[22] Filed: Sep. 13, 1982

Related U.S. Application Data

[62] Division of Ser. No. 328,274, Dec. 7, 1981, abandoned.

[51] Int. Cl.$^3$ ............... C07D 243/04; A61K 31/495
[52] U.S. Cl. ........................... 260/245.6; 260/243.3; 424/250; 544/370
[58] Field of Search ............... 260/245.6, 243.3; 544/370; 424/250

[56] References Cited

U.S. PATENT DOCUMENTS

| 3,539,573 | 11/1970 | Schmutz et al. | 260/263 |
| 3,933,794 | 1/1976 | Hester, Jr. et al. | 260/245.6 |
| 4,192,803 | 3/1980 | Wright et al. | 260/243.3 |
| 4,280,957 | 7/1981 | Walser et al. | 260/244 |
| 4,337,198 | 6/1982 | Sorg et al. | 260/243.3 |
| 4,391,808 | 7/1983 | Vlattas | 424/250 |

FOREIGN PATENT DOCUMENTS

| 3016 | 5/1979 | European Pat. Off. |
| 2077727 | 12/1981 | United Kingdom |

OTHER PUBLICATIONS

William B. Wright, Jr. et al. Derivatives of 11 (1-Piperazinyl-5H-pyrrolo[2,1-c][1,4]Benzodiazepine as Central Nervous System Agents, J. Med. Chem. 1980, 23,462–465.

Primary Examiner—Donald G. Daus
Assistant Examiner—Cecilia Shen
Attorney, Agent, or Firm—Norbert Gruenfeld

[57] ABSTRACT

5-Diazacycloalkylimidazo[1,2-c][1,3]benzodiazepines, for example compounds of the formula

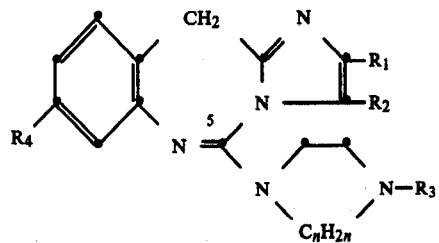

in which e.g., $R_1$, $R_2$ and $R_4$ are hydrogen, $R_3$ is methyl and $C_nH_{2n}$ is $CH_2CH_2$, have neurcleptic and/or antihistaminic activity. The synthesis, pharmaceutical compositions and methods of treatment utilizing such compounds are described.

4 Claims, No Drawings

5-DIAZACYCLOALKYLIMIDAZO[1,2-C][1,3]BENZODIAZEPINES

This is a division of application Ser. No. 328,274 filed on Dec. 7, 1981 now abandoned.

BACKGROUND OF THE INVENTION

Piperazinyl substituted ring fused benzodiazepines have been reported as antipsychotic/neuroleptic agents, e.g., clozapine (U.S. Pat. No. 3,539,573) and 11-piperazinyl-5H-pyrrolo[2,1-c][1,4]benzodiazepines (U.S. Pat. No. 4,192,803). On the basis of available literature, the 11H-imidazo[1,2-c][1,3]benzadiazepine ring system has not been described in the art.

SUMMARY OF THE INVENTION

The present invention concerns and has for its object the novel 5-diazacycloalkyl-imidazo[1,2-c][1,3]benzodiazepines and derivatives thereof. The invention also relates to processes for preparing said compounds, pharmaceutical compositions comprising said compounds, and application of said products in the treatment or management of psychoses (e.g. aggression, agitation and/or allergy) when administered, alone or in combination, to mammals.

The compounds of formula I exhibit valuable pharmacological properties, e.g. antihistaminic and psychotherapeutic e.g. antipsychotic (neuroleptic) effects. Said compounds, being essentially free of extrapyramidal effects, represent a novel chemical class of useful tranquilizers, primarily neuroleptic agents, essentially devoid of side effects e.g. dyskinesia and catalepsy seen with the classical major tranquilizers.

DETAILED DISCLOSURE OF THE INVENTION

Particularly the invention relates to compounds of formula I

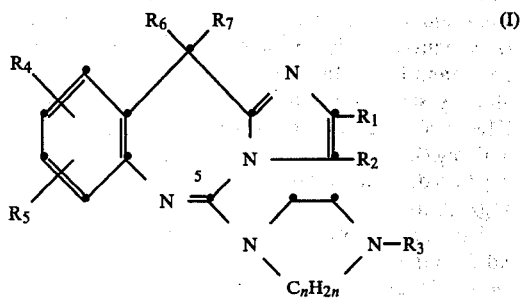

wherein $R_1$ and $R_2$ are hydrogen, lower alkyl, lower alkanoyl, halogen, cyano, carboxy, lower alkoxycarbonyl, carbamoyl, sulfamoyl, mono- or di-lower alkyl-(carbamoyl or sulfamoyl); $C_nH_{2n}$ is lower alkylene separating both nitrogen atoms by 2 or 3 carbon atoms; $R_3$ is hydrogen, lower alkyl, lower alkenyl, lower alkynyl, lower alkanoyl, aryl lower alkyl, lower alkoxycarbonyl, lower phenylalkoxycarbonyl or (hydroxy, lower alkanoyloxy, aryloxy or lower alkoxy) lower alkyl having at least two carbon atoms; $R_4$ and $R_5$ independently represent hydrogen, lower alkyl, lower alkoxy, lower alkylthio, halogen, trifluoromethyl, hydroxy, lower alkanoyloxy, sulfamoyl, mono- or di-lower alkylsulfamoyl; and $R_6$ and $R_7$ represent hydrogen or lower alkyl; the N-oxides, lower alkyl quaternary salts and pharmaceutically acceptable salts thereof.

Preferred embodiments of this invention relates to compounds of formula I wherein each of $R_1$ and $R_2$ is hydrogen, lower alkyl, cyano, carboxy, lower alkoxycarbonyl or carbamoyl; n represents the integer 2 to 4; $R_3$ is hydrogen, lower alkyl, lower alkoxycarbonyl or hydroxy lower alkyl of 2 to 4 carbon atoms; $R_4$ represents hyrogen, lower alkyl, lower alkoxy, lower alkylthio, halogen or trifluoromethyl; $R_5$ represents hydrogen; and $R_6$ and $R_7$ represent hydrogen or lower alkyl; the N-oxides; lower alkyl quaternary salts; or pharmaceutically acceptable salts thereof.

Highly preferred are compounds of formula I wherein $R_1$ and $R_2$ are hydrogen, methyl, ethyl, cyano, carboxy, alkoxycarbonyl of 1 to 3 carbon atoms in the alkoxy portion or carbamoyl; n represents the integer 2 or 3; $R_3$ is hydrogen, alkyl of 1 to 3 carbon atoms, alkoxycarbonyl of 1 to 3 carbon atoms in the alkoxy portion, hydroxyethyl or hydroxypropyl; $R_4$ represents hydrogen, methyl, methoxy, methylthio, chloro or trifluoromethyl; $R_5$ represents hydrogen; $R_6$ and $R_7$ represent hydrogen or methyl; the N-oxides; methyl quaternary salts; and pharmaceutically acceptable salts thereof.

Especially useful are compounds of formula II

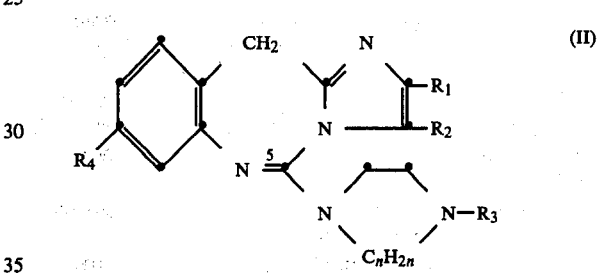

wherein $R_1$ and $R_2$ independently represent hydrogen or lower alkyl; $R_3$ represents hydrogen, lower alkyl or hydroxy lower alkyl wherein the hydroxy group is separated from the nitrogen atom by at least 2 carbon atoms; $R_4$ represents hydrogen, lower alkyl, lower alkoxy, lower alkylthio, halogen or trifluoromethyl; $C_nH_{2n}$ represents ethylene or propylene; the N-oxides; and pharmaceutically acceptable salts thereof.

Of particular interest are compounds of formula II wherein $R_1$ and $R_2$ independently represent hydrogen or methyl; $R_3$ represents hydrogen, methyl, ethyl, propyl, 2-hydroxyethyl or 3-hydroxypropyl; $R_4$ is hydrogen, methyl, methoxy, fluoro, chloro or trifluoromethyl; the N-oxides and pharmaceutically acceptable acid addition salts thereof.

Further preferred are compounds of formula II wherein $R_1$ and $R_2$ independently represent hydrogen or lower alkyl; $R_3$ represents hydrogen, lower alkyl or hydroxy lower alkyl wherein the hydroxy group is separated from the nitrogen atom by 2 carbon atoms; $R_4$ represents hydrogen, lower alkyl, halogen or trifluoromethyl; and $C_nH_{2n}$ represents ethylene or propylene; and pharmaceutically acceptable salts thereof.

Furthermore, the said compounds of formula II wherein $C_nH_{2n}$ represents ethylene are highly preferred.

The general definitions used herein have the meanings within the scope of the present invention as follows.

The term "lower" referred to above and hereinafter in connection with organic radicals or compounds respectively defines e.g. such alkyl, alkenyl and alkynyl radicals with up to and including 7, preferably up and including 4 and advantageously one or two carbon atoms.

Halogen is preferably fluoro or chloro, but may also be bromo or iodo.

A lower alkyl group or such present in said alkoxy, alkylthio or other alkylated groups, is above all methyl, but also ethyl, n- or i-(propyl, butyl, pentyl, hexyl or heptyl), e.g. 2-methylpropyl or 3-methylbutyl.

Lower alkenyl is preferably allyl.

Lower alkynyl is preferably propargyl.

Aryl lower alkyl is preferably benzyl, 1-, 2- or 3-phenylpropyl, 1- or 2-phenylethyl, said radicals being optionally substituted on the phenyl ring preferably by e.g. halogen, lower alkoxy or lower alkyl.

A lower alkoxy group preferably contains 1 to 4 carbon atoms and represents for example ethoxy, propoxy, isopropoxy or advantageously methoxy.

A lower alkylthio group preferably contains 1 to 4 carbon atoms and represents for example ethylthio, propylthio or advantageously methylthio.

The term "acyl" represents lower alkanoyl, lower alkoxy carbonyl, carbamoyl, sulfamoyl, mono- or di-lower alkyl (carbamoyl or sulfamoyl), halosulfonyl, lower phenylalkoxycarbonyl and the like.

Lower alkanoyl is preferably acetyl or propionyl. Lower alkanoyloxy is preferably acetyloxy or propionyloxy.

A lower alkoxycarbonyl, mono- or dialkyl (carbamoyl or sulfamoyl) group is preferably ethoxycarbonyl, methoxycarbonyl; mono- or dimethyl(carbamoyl or sulfamoyl).

A lower phenylalkoxycarbonyl group represents preferably benzyloxycarbonyl.

A lower alkylene group $C_nH_{2n}$ is especially ethylene; but also 1,2- or 1,3-propylene, 1,2-, 1,3- or 2,3-butylene; thus forming with both adjacent nitrogen atoms a piperazinyl or homopiperazinyl moiety.

A lower hydroxyalkyl group is preferably 2-hydroxy(ethyl or propyl), 3-hydroxy-(propyl or butyl) or 4-hydroxybutyl.

A lower alkanoyloxy lower alkyl group represents preferably lower alkanoyloxy (ethyl, propyl or butyl), e.g. 2-acetyloxy- or 2-propionyloxy (ethyl, propyl or butyl), 3-acetyloxy- or 3-propionyloxy-(propyl or butyl), 4-acetyloxy- or 4-propionyloxybutyl and the like.

A lower alkoxy lower alkyl group represents preferably lower alkyloxy-(ethyl, propyl or butyl), e.g. 2-methoxy- or ethoxy-(ethyl, propyl or butyl), 3-methoxy- or 3-ethoxy(propyl or butyl), 4-methoxy- or 4-ethoxybutyl and the like.

An aryloxy lower alkyl group represents preferably phenyloxy-(ethyl, propyl or butyl), said radicals being optionally substituted on the phenyl ring preferably by e.g. halogen, lower alkoxy or lower alkyl.

Lower alkyl quaternary salts of compounds of formula I are preferably, e.g. methyl, ethyl or propyl quaternary salts derived from reactive esters of lower alkanols having preferably from 1 to 4 carbon atoms, e.g. methanol, ethanol or propanol. The anions of said quaternary salts are preferably those corresponding to pharmaceutically acceptable acids such as halide, e.g. bromide or iodide; sulfate; or lower alkylsulfonate, e.g. methylsulfonate.

Although N-oxides or lower alkyl quaternary salts of compounds of formula I may represent such functionalized at one or more of any of the depicted ring nitrogen atoms in formula I, said N-oxides, lower alkyl quaternary salts of the compounds of formula I are preferably derived from those wherein $R_3$ is lower alkyl, aryl lower alkyl, or (hydroxy, lower alkanoyloxy, aryloxy or lower alkoxy) lower alkyl having at least 2 carbon atoms and wherein only the nitrogen atom bearing said $R_3$ substituent is thus functionalized.

Said compounds of Formula I form acid addition salts, which are preferably such of pharmaceutically acceptable inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. acetic, propionic, succinic, glycolic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, benzenesulfonic, p-toluenesulfonic, naphthalenesulfonic, sulfanilic or cyclohexylsulfamic acid.

Compounds of formula I with $R_1$ and/or $R_2$ being carboxy also form pharmaceutically acceptable salts with bases which are preferably metal or ammonium salts, more particularly alkali or alkaline earth metal salts, e.g., the sodium, potassium, magnesium or calcium salt; or advantageously easily crystallizing ammonium salts derived from ammonia or organic amines, such as mono- di- or tri-lower (alkyl, cycloalkyl or hydroxyalkyl)amines, lower alkylenediamines or lower hydroxyalkylamines, cyclic amines or (aralkyl)alkylammonium bases, e.g., methylamine, diethylamine, triethylamine, dicyclohexylamine, triethanolamine, ethylenediamine, tris-(hydroxymethyl) methylamine, piperidine, morpholine or benzyltrimethylammonium hydroxide.

The compounds of the invention exhibit valuable pharmacological properties, psychoactive, e.g. neuroleptic, as well as antiallergic, e.g. antihistaminic effects. Such are demonstrable in animal tests using advantageously mammals, e.g. mice, rats, guinea pigs or monkeys, as test objects. Said compounds can be applied to them enterally or parenterally, advantageously orally, or subcutaneously, intravenously or intraperitoneally, for example, within gelatin capsules or in the form of starchy suspensions or aqueous solutions respectively. The applied dosage may range between about 0.1 and 100 mg/kg/day, preferably between about 0.5 and 50 mg/kg/day, advantageously between about 1 and 30 mg/kg/day.

Said neuroleptic properties can be demonstrated in adult rats or squirrel monkeys, which were trained to press a lever to avoid the onset of an electric foot shock. Each lever press postpones the shock for 30 seconds. Whenever the animal fails to press the lever once within said period, brief (0.5 sec.) shocks are delivered at 15 second intervals until the animal again presses the lever. Under control conditions the animals press the lever at a moderately steady rate and seldom receive more than five or six shocks during a 25-minute (rats) and up to 4-hour experimental session. Said compounds evaluated for neuroleptic activity, are administered to the animals 30, 90, 210 minutes prior to the experimental session and block the learned conditioned avoidance behavior, manifested by a decrease in avoidance responding with a marked increase in shocks taken by the animal. Both the avoidance responses and failures (shocks received) are recorded separately for evaluation.

Finally, said antihistaminic properties can be shown in vitro, e.g., according to Chasin et al., J. Neurochem.

22, 1031 (1974). Vesicles from a cell free preparation of guinea pig cerebral cortex are preincubated with $^3$H-adenine to form endogenous $^3$H-adenosine triphosphate. The vesicles are then incubated with 50 micromolar histamine to activate $^3$H-cyclic adenosine monophosphate synthesis in the absence or presence of the test compound at a concentration between 0.01 and 100 micromolar. When said compound is active, it inhibits the histamine activation of adenylate cyclase. The IC$_{50}$ represents the concentration at which histamine activation is inhibited by 50%.

Indicative of the antipsychotic utility of the compounds of this invention, e.g., the compound of example 1, namely 5-(4-methyl-1-piperazinyl)-11H-imidazol[1,2-c][1,3]benzodiazepine disrupts avoidance behavior, e.g. decreases avoidance responses in rats and monkeys at an oral dose of 30 mg/kg or lower.

Illustrative of the antihistaminic activity, 5-(4-methyl-1-piperazinyl)-11H-imidazo[1,2,-c][1,3]benzodiazepine, the compound of example 1, inhibits histamine activation of adenylate cyclase, with an IC$_{50}$ of about $1 \times 10^{-6}$M. Furthermore, the compound of example 1, an illustrative example of this invention, is essentially free of extrapyramidal side effects, e.g. dyskinesias and dystonias in the monkey, and shows only minimal α-adrenergic blocking activity in vitro.

Accordingly, the compounds of the invention are useful neuroleptic and antihistaminic agents, for example, in the treatment or management of psychotic manifestations, e.g., aggression, agitation, schizophrenia, and/or allergic conditions in mammals, including man. They are also useful intermediates in the preparation of other valuable products, especially of pharmacologically active compositions.

The compounds of the invention are prepared according to the following method:

(a) condensing a compound of formula III

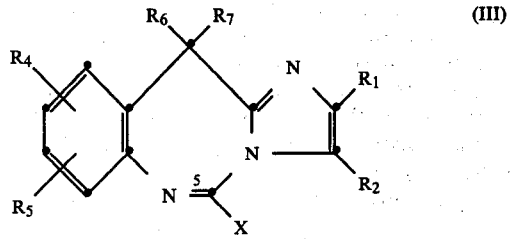

wherein X is halogen, lower alkoxy, lower alkylthio, cyanato or thiocyanato and the remaining symbols have meaning as defined for formula I; with a compound of formula IV or an alkali metal

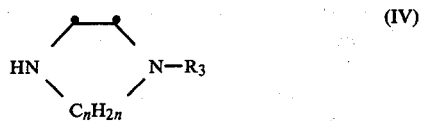

derivative thereof wherein R$_3$ has meaning as defined for formula I; and, if desired (b) converting any resulting compound into another compound of formula I.

Said condensation is advantageously carried out with an excess of the compound IV, or with equivalent amounts of said metal derivatives prepared in situ therefrom, preferably when X in formula III is halogeno, lower alkylthio or thiocyanato, advantageously and depending on the nature of said X, at temperatures between about 0° and 150°, and preferably in an appropriate solvent e.g. a lower alkanol such as amyl alcohol, dimethylformamide, hexamethylphosphoramide, toluene and the like. Said condensation of a compound of formula III with a compound of formula IV may also be carried out in the presence of an acid, e.g., a hydrohalic acid such as hydrochloric acid.

The novel 11H-imidazo[1,2-c][1,3]benzodiazepine intermediates of formula III wherein X is hydroxy or sulfhydryl are prepared according to ring closure methods, advantageously by condensing compounds of formula V

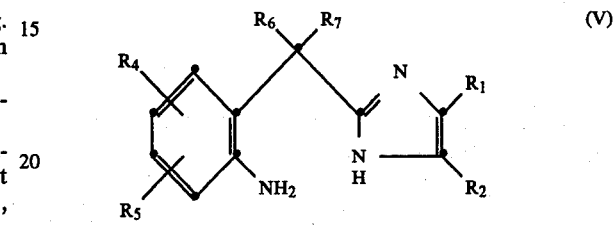

wherein R$_1$, R$_2$, R$_4$–R$_7$ have meaning as previously defined for formula I with reactive carbonic acid derivatives such as phosgene, thiophosgene, 1,1'-carbonyldiimidazole, cyanogen bromide, phenyl chloroformate and the like.

Compounds of formula III wherein X is hydroxy can be converted to compounds wherein X is sulfhydryl by conventional sulfurating agents, such as phorphorus pentasulfide.

Compounds of formula III wherein X is hydroxy or sulfhydryl can be further derivatized to compounds of formula III above wherein X is halogen, lower alkoxy, lower alkylthio, cyanato or thiocyanato analogous to the procedures illustrated by the examples herein.

Starting materials of formula V are preferably prepared by reduction of the corresponding variously substituted 2-(o-nitrobenzyl)imidazoles, which are in turn preferably prepared from the correspondingly substituted o-nitrobenzylnitriles and 2-aminoacetals (or ketals), e.g. aminoacetaldehyde dimethyl acetal, by known methods illustrated in the examples herein.

The compounds of the invention are also prepared according to the following scheme:

(a) cyclizing a compound of formula VI

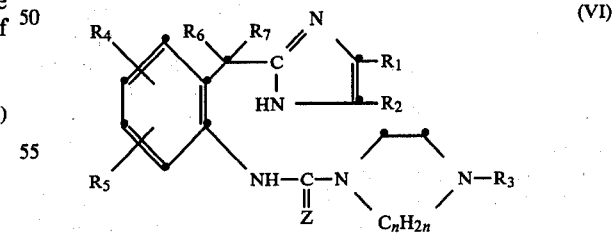

wherein Z is oxygen, sulfur, or NH, and the other symbols have the above-given meaning, under dehydrating, dehydrosulfurating or deamination conditions to a compound of formula I; and if desired (b) converting any resulting compound into another compound of formula I.

Said cyclization is preferably carried out at temperatures between 0° and 120° and advantageously in an inert solvent, such as acetonitrile and toluene, with a reagent such as cyanogen bromide, phosphorus pentachloride, phosphorus oxychloride and the like, with or without basic catalysts such as triethylamine or potassium carbonate.

The starting materials of Formula VI can be obtained from precursors of Formula III or tautomers thereof, wherein X is hydroxy, thio or amino by condensing them with compounds of Formula IV in the presence or absence of other bases, e.g. those listed above, preferably in an inert solvent, such as methylene chloride or toluene at temperatures between 0° and 150° advantageously between 10° and 50°. The ring opening reaction is preferably carried out at low temperature to minimize side reactions when $R_1$ and $R_2$ represent functional groups.

Alternately, starting materials of formula VI, wherein $R_3$ is alkanoyl, alkoxycarbonyl or phenylalkoxycarbonyl, are prepared by condensing a compound of formula V above with a compound of formula VII wherein Y' represents halocarbonyl, halothiocarbonyl or cyano, and $R_3'$ represents lower alkanoyl, lower alkoxycarbonyl or lower phenylalkoxycarbonyl, preferably in an inert solvent, at temperatures between about 0° and 150°, with or without basic catalysts such as triethylamine or potassium carbonate.

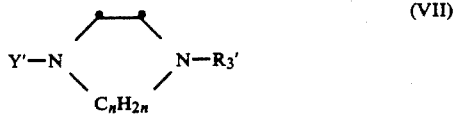

(VII)

Starting materials of formula VII are preferably obtained by reacting compounds of formula IV wherein $R_3$ represents lower alkanoyl, lower alkoxycarbonyl or lower phenylalkoxycarbonyl, or advantageously e.g. the N-trimethylsilyl derivative thereof, with phosgene, thiophosgene, cyanogen bromide or the like in an inert solvent such as ethyl ether, methylene chloride or dimethoxyethane at temperatures of about −70° to +50° with or without basic catalysts such as triethylamine or potassium carbonate.

The compounds of the invention so obtained can be converted into other compounds of Formula I according to known methods. Thus, for example, those with $R_3$ being hydrogen or alkali metal, e.g., sodium or lithium salts thereof, can be reacted with substituted oxiranes, such as ethylene oxide, or reactive esters of unsubstituted or correspondingly substituted aliphatic or araliphatic alcohols such as methanol, ethanol, methoxyethanol, phenoxyethanol, allyl alcohol, propargyl alcohol, e.g. such esterified by a strong inorganic or organic acid, above all hydrohalic acids, e.g. hydrochloric, hydrobromic or hydriodic acid; sulfuric or an aromatic sulfonic acid, e.g. p-toluene or m-bromobenzene sulfonic acid, in order to obtain the corresponding N-substituted compounds or quaternaries respectively, depending on the molar amount of the alkylating agent employed. Intermediates of formula I wherein $R_3$ is alkali metal or alkali metal derivatives of compounds of formula IV are obtained by metallation with reactive organometallic agents such as lithium diisopropylamide, with alkali metal alkoxides such as sodium methoxide, or alkali metal hydrides such as sodium or potassium hydride.

Unsaturated compounds, such as those with $R_3$ being lower alkenyl, lower alkynyl may be hydrogenated with catalytically activated hydrogen to obtain compounds wherein $R_3$ is the corresponding lower alkyl.

Conversely, resulting N-alkylated compounds can be converted into N-unsubstitued compounds, e.g. by catalytic hydrogenolysis of N-benzyl compounds, or reaction of N-lower alkyl derivatives with lower alkyl haloformates, e.g. ethyl chloroformate, to yield N-acyl derivatives which, in turn, may be hydrolyzed to said unsubstituted compounds, those with $R_3=H$, for example with aqueous bases, such as alkali metal hydroxides, e.g. aqueous sodium hydroxide solution.

Compounds of formula I wherein $R_3$ is hydroxyalkyl can also be prepared by first reacting corresponding compounds of Formula I, wherein $R_3$ represents hydrogen, with reactive derivatives of corresponding glycols, glycolic acids or dicarboxylic acids, such as lower alkyl esters, halides or anhydrides thereof, or reactive esters or said glycols or glycolic acids derivatives, for example with hydrohalic or aromatic sulfonic acids, 1,2-dibromoethane or -propane, ethyl bromoacetate or -propionate, ethyl tosyloxyacetate; diethyl oxalate or malonate or ethyl oxalyl chloride. The intermediates so obtained are either hydrolyzed or reduced with simple or complex light metal hydrides such as lithium aluminum hydride, alone or with diborane to compounds of formula I wherein $R_3$ is hydroxyalkyl.

Compounds of formula I wherein $R_3$ is lower alkyl, e.g. methyl can be prepared by reacting the corresponding compounds of formula I wherein $R_3$ represents hydrogen with lower alkyl or phenyl lower alkyl haloformates, such as ethyl chloroformate, to obtain compounds of formula I wherein $R_3$ is lower alkoxycarbonyl or lower phenylalkyloxycarbonyl, and reducing said acyl derivatives with simple or complex light metal hydrides such as lithium aluminum hydride, sodium tri-t-butoxy or bis-(2-methoxyethoxy) aluminum hydride.

N-acylated derivatives of formula I wherein $R_3$ is lower alkanoyl can preferably be obtained from compounds of Formula I with $R_3$ being hydrogen and corresponding reactive carboxylic acid derivatives, e.g., halides, simple or activated esters, such as alkyl or cyanoalkyl esters or anhydrides. These in turn can be reduced as above to the compounds of formula I wherein $R_3$ is lower alkyl. Compounds of formula I wherein $R_3$ is hydroxy lower alkyl may be acylated as above to the compounds wherein $R_3$ is lower alkanoyloxy lower alkyl.

Compounds of Formula I with $R_1$ and/or $R_2$ being hydrogen, may be converted to the corresponding compounds with $R_1$ and/or $R_2$ being halogen or acyl, e.g. by halogenation, preferably with chlorine in acetic acid or under Friedel-Crafts conditions by acylation with e.g. a lower alkanoyl halide, a lower alkyl haloformate, a trihaloacetyl halide or a halosulfonic acid optionally followed by treatment with an alkali metal lower alkoxide, hydroxide or amide. Any resulting carboxylic or sulfonic acid derivatives may then be hydrolyzed in known fashion, preferably under alkaline conditions and/or amidized with ammonia, mono- or di-lower alkylamines; the resulting primary carboxamides may in turn be dehydrated to the corresponding nitriles according to conventional methods.

Tertiary amines with $R_3$ being, e.g. lower alkyl, aryl lower alkyl and the like, can be converted into the N-oxides, for example with hydrogen peroxide or organic peracids, such as lower peralkanoic or perbenzoic acids, e.g. peracetic or m-chloroperbenzoic acid, advantageously at temperatures at or below room temperature with the latter, or up to 100° with hydrogen peroxide in the presence of lower alkanoic acids, e.g. acetic acid. If only a mono N-oxide is desired, care should be taken in order to prevent further oxidation.

Finally, the compounds of the invention are either obtained in the free form, or as a salt thereof. Any resulting base can be converted into a corresponding acid addition salt, preferably with the use of a pharmaceutically acceptable acid or anion exchange preparation, or any resulting salt can be converted into the corresponding free base, for example, with the use of a stronger base, such as a metal or ammonium hydroxide or a basic salt, e.g. an alkali metal hydroxide or carbonate, or a cation exchange preparation. Said acid addition salts are preferably such of pharmaceutically acceptable inorganic or organic acids described previously.

Compounds of formula I with $R_1$ and/or $R_2$ being carboxy can be converted into the corresponding metal or ammonium salts by e.g. treatment with the alkaline or alkaline earth metal hydroxides or carbonates, ammonia or the amines listed previously.

These or other salts, for example, the picrates, can also be used for purification of the bases obtained; the bases are converted into salts, the salts are separated and the bases are liberated from the salts.

In view of the close relationship between the free compounds and the compounds in the form of their salts, whenever a compond is referred to in this context, a corresponding salt is also intended, provided such is possible or appropriate under the circumstances.

In case mixtures of geometrical or optical isomers of the above compounds, e.g. I to VII are obtained, these can be separated into the single isomers by methods in themselves known, e.g. by fractional distillation, crystallization and/or chromatography. Racemic products can likewise be resolved into the antipodes, for example, by separation of diastereomeric salts thereof, e.g. by the fractional crystallization of the salts formed with d- or l-tartaric acid, mandelic acid, cinchonidine and the like.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds, indicated above as being especially valuable, e.g. those of Formula II.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, or effervescent mixtures and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressures and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 Kg weight may contain between about 25 and 200 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mm Hg.

EXAMPLE 1

5-(4-methyl-1-piperazinyl)-11H-imidazo[1,2-c][1,3]benzodiazepine

Amyl alcohol (5100 ml) and 918.35 g (9.17 moles) of N-methylpiperazine were charged into a 12 liter 3-necked reaction flask fitted with a Dean-Stark adapter. The solution was stirred under nitrogen atmosphere and 989 ml of 10N ethanolic hydrogen chloride solution were added rapidly. The reaction mixture was heated to reflux and the distillate was collected in the Dean-Stark adapter. When the temperature of the reaction mixture reached 131° the Dean-Stark adapter was removed and an additional 918.35 g (9.17 moles) of N-methylpiperazine followed by 1045.0 g (4.56 moles) of 5-methylthio-11H-imidazo[1,2-c][1,3]benzodiazepine were added. The mixture was heated at reflux under nitrogen atmosphere for 20 hours. Amyl alcohol was then removed under reduced pressure at a water bath temperature of 80°. The viscous residual oil was dissolved in 10,000 ml of dichloromethane, washed with 3×4,000 ml of 4N sodium hydroxide and 6×4,000 ml of water. The dichloromethane solution was then extracted with 3×2,000 ml of 6N hydrochloric acid. The aqueous solution was back washed with 2×2,000 ml of dichloromethane, treated with 100 g of activated carbon and filtered. The clear filtrate was adjusted to pH 9–10 with 1,500 ml of ammonium hydroxide solution (29%). The oil which separated was extracted with 3×4,000 ml of dichloromethane, the extracts were dried over 1,000 g of sodium sulfate and the solvent removed at reduced pressure with a water bath temperature of 60°. An oil was obtained which rapidly solidified and after drying further (5 mm Hg/40°) yielded crude product, m.p. 113°–120°. The crude product was dissolved in 8,000 ml of hot (60°–70°) isopropanol. The solution was decolorized with 200 g of activated carbon and filtered. To this solution was added a solution of 760.7 g (8.28 moles) of maleic acid in 2,500 ml of warm (30°) isopropanol and the maleate salt began to precipitate. The suspension was stirred overnight at ambient temperature to complete crystallization and the solid was collected by filtration. The product was washed with 3×500 ml of cold isopropanol and dried (0.5 mm/50°). This was recrystallized from ethanol, the resulting product was washed first with ethanol and then with ether and then dried to give 5-(4-methyl-1-piperazinyl)-11H-imidazo[1,2-c][1,3]benzodiazepine monomaleate, m.p. 204°-205° (dec).

A solution of 2,246 g of the above maleate salt in 9000 ml of water was treated with 100 g of activated carbon and filtered. The aqueous solution was adjusted to pH9 with 1000 ml of 29% ammonium hydroxide and the free base separated as an oil. The oil was extracted with 3×2000 ml of dichloromethane, the extract was dried over sodium sulfate, filtered and the solvent was removed under reduced pressure at a water bath temperature of 40°. The solid obtained was recrystallized from 14,130 ml of heptane. The light yellow solid was collected and washed with 2×500 ml of heptane and dried (0.01 mm/50°) to give 5-(4-methyl-1-piperazinyl)-11H-imidazo[1,2-c][1,3]benzodiazepine, m.p. 123°-4°, the compound of formula II wherein $R_1$, $R_2$ and $R_4$ are hydrogen, $C_nH_{2n}$ is $CH_2CH_2$ and $R_3$ is methyl.

The starting material was prepared as follows:

Absolute ethanol (24,000 ml) and 3,240 g (60.0 moles) of sodium methoxide were charged into a 20 gallon reaction flask. The solution was stirred under nitrogen while a solution of 8228.4 g (60.0 moles) of o-nitrotoluene and 8768.4 g (60.0 moles) of diethyl oxalate was added all at once. The resulting solution was heated at reflux for 25 minutes, cooled to 60° with an ice-bath and 18,000 ml of water were cautiously added. Heat was then applied and the mixture was held at the reflux temperature for 1 hour. Most of the ethanol was then removed. The turbid solution was cooled at 50° and a solution of 4,140 g (59.6 moles) of hydroxylamine hydrochloride in 6,000 ml of water was added all at once. The temperature was maintained at 50°, the pH was adjusted to 7.0 with 6,000 ml of 10N sodium hydroxide solution and the reaction mixture stirred overnight at ambient temperature. The suspension was cooled to 10° and the pH was adjusted to 1.0 with 6,000 ml of 12N hydrochloric acid. The stirring was continued overnight at 10° to complete the liberation of the free acid. The solid was collected, washed with 6×4,000 ml of water, air dried overnight and suspended in 20,000 ml of toluene. The suspension was stirred for 1 hour under nitrogen atmosphere. The product was collected, washed with 4×2,000 ml of toluene followed by 4×2,000 ml of petroleum ether and dried (5 mm Hg/60°) to give 2-nitrophenylpyruvic acid oxime, m.p. 158°-60° (dec).

Water (50,000 ml), 2,940 ml of glacial acetic acid and (22.22 moles) of 2-nitrophenylpyruvic acid oxime were charged into a 20 gallon reactor. The stirred suspension was heated over two hours under nitrogen atmosphere to 90° and this temperature was maintained for 2 hours. The dark solution was allowed to cool slowly and was stirred overnight at ambient temperature. The suspension was extracted with 5×4,000 ml of methylene chloride, washed with 3×3,000 ml of water, dried over magnesium sulfate and filtered. The filtrate was treated with activated carbon, filtered and the solvent was removed under reduced pressure. The solid residue was recrystallized from 1,000 ml of isopropanol to give 2-nitrophenylacetonitrile, m.p. 82°-84°.

Absolute ethanol (2,250 ml) and 1,500 g (9.25 moles) of o-nitrophenylacetonitrile were charged into a 22 liter flask. The suspension was cooled to 5°-10° and hydrogen chloride was bubbled into the mixture for 2.5 hours. The reaction mixture was stirred at 10° under nitrogen atmosphere overnight. It was then diluted with 16,000 ml of ether and stirred for 1 hour; the solid was collected by filtration, washed with 4×1,000 ml of ether dried (5 mm Hg/40°) to give ethyl 2-(2-nitrophenyl)acetimidate hydrochloride, m.p. 122°-123° (dec).

Ethanol (2,200 ml) and 5,156 g (8.81 moles) of ethyl 2-(2-nitrophenyl)acetimidate hydrochloride were charged into a 22 liter flask. The suspension was stirred under nitrogen at room temperature and 1022.9 g (9.73 moles) of aminoacetaldehyde dimethylacetal were added all at once. The mixture was stirred for 1 hour and 1,693 ml of 12N hydrochloric acid were added all at once to cause a gentle exotherm (to 40°). Heat was then applied and the temperature was maintained at 70°-80° for 30 minutes. The solution was cooled to 20° (ice-water bath) and diluted with 2,700 ml of 10N sodium hydroxide solution to precipitate the product. The suspension was stirred at 10° for 1 hour under nitrogen atmosphere, the solid collected by filtration and washed with 3×2,000 ml of water to give 2-(2-nitrobenzyl)-imidazole, m.p. 155°-7°.

50% Aqueous ethanol (5,672 ml) and 2,890 g (14.22 moles) of 2-(2-nitrobenzyl)imidazole were charged into a 22 liter flask. The suspension was stirred under nitrogen atmosphere and 2,400 g (42.97 moles) of iron powder (100 mesh) were added all at once. The mixture was then warmed to 70° and a solution of 1.7 ml of 12N hydrochloric acid in 8.3 ml absolute ethanol were added. A vigorous exotherm resulted and a strong reflux occurred that persisted for 1.5 hours. When the exotherm subsided, a mixture of 290 ml of 12N HCl and 1400 ml of absolute ethanol were added over 30 minutes. Heat was applied and the mixture was refluxed for 2 hours, diluted with 6,500 ml of absolute ethanol and adjusted to pH 8-9 with 700 ml of 10N sodium hydroxide. The suspension was stirred for 1 hour and filtered. The cake was washed with 1,000 ml of absolute ethanol, the filtrates were combined and the solvent was removed. The remaining solid was then suspended in 10,000 ml of water, stirred under nitrogen atmosphere for two hours, collected, washed with 2,000 ml of water, and dried to yield 2-(2-aminobenzyl)imidazole, m.p. 153°-155°.

Dichloromethane (42,000 ml) and 5,120 g (50.65 moles) of triethylamine were charged into a 20 gallon flask. The solution was stirred under nitrogen atmosphere and 4,370 g (25.23 moles) of 2-(2-aminobenzyl)imidazole were added. The suspension was cooled to 0°-5° and 3,421 g (29.75 moles) of 85% thiophosgene in carbon tetrachloride were added over 3 hours, during which time the reaction temperature rose slowly to 15°. The suspension was then stirred at 10° for 4 hours and at ambient temperature overnight. The precipitated product was collected, washed with 2×3000 ml of dichloromethane and 5×4000 ml of water, and dried (5 mm Hg/60°) to give 11H-imidazo[1,2-c][1,3]benzodiazepine-5(6H)-thione, m.p. 182°-183°.

Absolute ethanol (20,000 ml) was charged into a 20 gallon flask and stirred under nitrogen atmosphere; 517.62 g (9.58 moles) of sodium methoxide were added. After stirring for 30 minutes there was complete solution and 2,063 g (9.58 moles) of 11H-imidazo[1,2-c][1,3]benzodiazepine-5(6H)-thione were added. There was complete solution after stirring at room temperature for 1 hours. The solution was then cooled to 1°, and 1,360 g (9.58 moles) of methyl iodide were added over 30 minutes. The reaction mixture was stirred at 5° for 4 hours and at ambient temperature overnight. The turbid solution was then cooled to 5° and diluted with 50,000 ml of water. The resulting suspension was stirred for 4 hours at 5°. The solid was collected, and dried (5 mm Hg/60°) to give 5-methylthio-11H-imidazo[1,2-c][1,3]benzodiazepine, m.p. 87°-8°.

Similarly prepared from 4-chloro-2-nitrophenylacetonitrile was 8-chloro-11H-imidazo[1,2-c][1,3]benzodiazepine-5(6H)-thione, m.p. 200°-201° and 8-chloro-5-methylthio-11H-imidazo[1,2-c][1,3]benzodiazepine hydrochloride, m.p. 255°-7°.

The following starting materials are similarly prepared from the correspondingly substituted 2-nitrophenylacetonitriles:
  8-methyl-5-methylthio-11H-imidazo[1,2-c][1,3]benzodiazepine;
  8-fluoro-5-methylthio-11H-imidazo[1,2-c][1,3]benzodiazepine;
  8-methoxy-5-methylthio-11H-imidazo[1,2-c][1,3]benzodiazepine.

EXAMPLE 2

To a suspension of 2.46 g of 1-[2-(2-imidazolylmethyl)phenylcarbamoyl]-4-methylhomopiperazine in 19.4 ml of phosphorus oxychloride was added at once 1.66 g of phosphorous pentachloride and the mixture was stirred at room temperature for 4 hours. The mixture was evaporated to dryness, the residue was suspended in 45.2 ml of methylene chloride, the suspension was cooled to 0° and 21.4 ml of triethylamine were added dropwise with stirring over a period of 15 minutes. The mixture was allowed to warm up to room temperature, stirred for 1.5 hours and poured into 10% aqueous potassium carbonate. The methylene chloride layer was separated, the aqueous layer was washed with methylene chloride and the combined methylene chloride extracts were dried over MgSO$_4$, decolorized with charcoal and evaporated to dryness. The residue was purified by column chromatography with 50 g of silica gel, using methylene chloride-methanol-conc. ammonium hydroxide (300:50:1) as eluent to give 5-(4-methyl-1-homopiperazinyl)-11H-imidazo[1,2-c][1,3]benzodiazepine as an oil. This free base was dissolved in acetone and treated with maleic acid to give 5-(4-methyl-1-homopiperazinyl)-11H-imidazo[1,2-c][1,3]benzodiazepine monomaleate, m.p. 160°-163°.

5-(4-Methyl-1-piperazinyl)-11H-imidazo[1,2-c][1,3]benzodiazepine monomaleate of example 1 was similarly prepared from 1-[2-(2-imidazolylmethyl)-phenylcarbamoyl]-4-methylpiperazine.

The starting materials were prepared as follows:

A solution of 32.4 g of phenyl chloroformate in 100 ml of acetonitrile was added dropwise under nitrogen while stirring to a mixture of 34.6 g of 2-(2-aminobenzyl)imidazole and 71 g of triethylamine in 600 ml of acetonitrile at room temperature. After addition was complete, the reaction mixture was heated under reflux for 12 hours, and allowed to cool to room temperature. Water (150 ml) was added, the mixture was stirred at room temperature for 0.5 hour and cooled to 5°. The resulting precipitate was filtered off, washed first twice with 50 ml of water, then 3 times with 33 ml of cold acetone and dried to give 11H-imidazo[1,2-c][1,3]benzodiazepin-5-(6H)-one, m.p. 255°-7°.

Alternately, 0.75 g of 1,1'-carbonyldiimidazole was added at once to a suspension of 0.79 g of 2-(2-aminobenzyl)imidazole in 38 ml of methylene chloride and the mixture was stirred at room temperature overnight. The resulting precipitate was collected and recrystallized from methylene chloride to give the crude 11H-imidazo[1,2-c][1,3]benzodiazepin-5(6H)-one, m.p. 238°-40°.

In analogous fashion, or by using phosgene as the reagent for cyclization, the following intermediates are obtained:
  (a) 2,3-dimethyl-11H-imidazo[1,2-c][1,3]benzodiazepin-5-(6H)-one;
  (b) 8-chloro-11H-imidazo[1,2-c][1,3]benzodiazepin-5(6H)-one;
  (c) 8-methyl-11H-imidazo[1,2-c][1,3]benzodiazepin-5-(6H)-one;
  (d) 8-methoxy-11H-imidazo[1,2-c][1,3]benzodiazepine-5-(6H)-one.

To a suspension of 0.76 g of 11H-imidazo[1,2-c][1,3]benzodiazepin-5(6H)-one in 9 ml of methylene chloride was added at once 0.41 g of N-methylhomopiperazine and the mixture was stirred at room temperature for 24 hours. The reaction mixture was filtered and the filtrate was evaporated to dryness. Recrystallization of the residue from methylene chloride-ether gave 1-[2-(2-imidazolylmethyl)phenylcarbamoyl]-4-methylhomopiperazine, the compound of formula VI wherein $R_1$, $R_2$, $R_4$-$R_7$ are hydrogen, $C_nH_{2n}$ is $(CH_2)_3$, $R_3$ is methyl and Z is oxygen, melting at 139°-143°.

Similarly prepared from N-methylpiperazine was 1-[2-(2-imidazolylmethyl)phenylcarbamoyl]-4-methylpiperazine, m.p. 172°-4°.

The following compounds are prepared according to the above procedures:
  1-[2-(4,5-dimethyl-2-imidazolylmethyl)phenylcarbamoyl]-4-methylpiperazine; and
  1-[2-(2-imidazolylmethyl)-5-chlorophenylcarbamoyl]-4-methylpiperazine.

EXAMPLE 3

A solution of 2.4 g of 5-cyanomercapto-11H-imidazo[1,2-c][1,3]benzodiazepine in 5 ml of hexamethylphosphoramide was cooled to −5° and 2.1 g of N-methylpiperazine was added dropwise with efficient mechanical stirring and under nitrogen, over a period of 5 minutes. Stirring was continued for 10 minutes at −5° and another 10 minutes after removal of the cooling bath. The mixture was diluted with 100 ml of ethyl acetate and the solution washed twice with brine, dried (MgSO$_4$), and evaporated to dryness. To the residue, a solution of 1.2 of maleic acid in 3 ml acetone was added and the mixture was diluted with ether. The crude product crystallized, m.p. 183°-186°, and was recrystallized to give the 5-(4-methyl-1-piperazinyl)-11H-imidazo[1,2-c][1,3]benzodiazepine monomaleate of example 1.

The starting material was prepared as follows:

Sodium hydride (50% in mineral oil, 1.44 g,) was washed with dry ether and suspended in 100 ml of dry tetrahydrofuran; 6.45 g of 11H-imidazo[1,2-c][1,3]benzodiazepine-5(6H)-thione was added in portions to the suspension of sodium hydride, with stirring and under nitrogen, over a period of 2 minutes. The mixture was stirred at room temperature for 1.5 hours. The white suspension, which was formed by the end of this time, was cooled to 0° and 3.5 g of cyanogen bromide dissolved in 10 ml of dry tetrahydrofuran was added dropwise. The mixture was stirred at room temperature for 0.5 hour and evaporated under reduced pressure at 45°. The residue was dissolved in methylene chloride, the solution was washed with water, dried (MgSO$_4$), decolorized with charcoal, and evaporated to a small volume. 5-Cyanomercapto-11H-imidazo[1,2-c][1,3]benzodiazepine, m.p. 111°–113°, crystallized on dilution with ether.

EXAMPLE 4

To a solution of 8.9 g of 1-[2-(2-imidazolylmethyl)-phenylthiocarbamoyl]-4-ethoxycarbonylpiperazine in 70 ml of acetonitrile, cooled to 0°, was added 2.4 g of solid potassium carbonate while stirring, followed by dropwise addition of a solution of 2.5 g of cyanogen bromide in 10 ml of acetonitrile; the mixture was allowed to warm up to room temperature overnight. The solids were filtered off, washed with ethyl acetate, and the filtrate was evaporated to dryness. The residue was dissolved in methylene chloride, the solution was washed with water, dried over M$_g$SO$_4$, decolorized with charcoal and evaporated to dryness. The residue was chromatographed with 250 g of silica gel using ethyl acetate-methanol (9:1) as eluant to give 5-(4-ethoxycarbonyl-1-piperazinyl)-11H-imidazo[1,2-c][1,3]benzodiazepine, m.p. 137°–139°.

The starting material was prepared as follows:

A solution of 20 g of 1-ethoxycarbonylpiperazine in 400 ml dry tetrahydrofuran was cooled to −65° and 61.5 ml of 2.1M solution of n-butyllithium in hexane was added dropwise over a period of 15 minutes. The mixture was stirred for 15 minutes and a solution of 16.44 ml of chlorotrimethylsilane in 68 ml of tetrahydrofuran was added dropwise over a period of 15 minutes. The mixture was then allowed to warm up to room temperature overnight and evaporated to dryness. Ethyl ether was added, the solids were filtered off, the filtrate was evaporated to dryness and the residue was distilled to give 1-ethoxycarbonyl-4-trimethylsilylpiperazine, b.p. 102°–107°/0.1 mm/Hg.

To a solution of 4.66 ml of 85% thiophosgene in 200 ml of ethyl ether, cooled to −76° was added, while stirring and under nitrogen, a solution of 7 g of 1-ethoxycarbonyl-4-trimethylsilylpiperazine in 35 ml of ethyl ether over a period of 20 minutes. The mixture was allowed to warm up to room temperature overnight. The suspension was filtered and the filtrate was evaporated to dryness. The residue was crystallized from methylene chloride-hexane to give 4-ethoxycarbonyl-1-piperazinylthiocarbonyl chloride, m.p. 107°–111°.

To a suspension of 3.8 g of 2-(2-aminobenzyl)imidazole in 38 ml of tetrahydrofuran and 3.23 ml of triethylamine was added dropwise a solution of 5.5 g of 4-ethoxycarbonyl-1-piperazinyl-thiocarbonyl chloride in 10 ml of methylene chloride at room temperature. The mixture was stirred for 1 week and the suspension filtered. The filtrate was washed with first 10% aqueous potassium carbonate, then with water, dried and evaporated to dryness to give amorphous 1-[2-(2-imidazolylmethyl)phenylthiocarbamoyl]-4-ethoxycarbonylpiperazine, characterized by NMR.

EXAMPLE 5

According to the methods illustrated by the previous examples, the following compounds of formula II wherein R$_1$ and R$_2$ represent hydrogen, and C$_2$H$_{2n}$ represents CH$_2$CH$_2$ were obtained from equivalent amounts of the corresponding starting materials.

| No. | R$_3$ | R$_4$ | Salt | m.p. |
|---|---|---|---|---|
| 1 | CH$_2$CH$_2$OH | H | — | 143-4° |
| 2 | CH$_2$CH$_2$OH | Cl | HCl | 225° dec. |
| 3 | CH$_3$ | Cl | 2HCl | 226-8° dec. |
| 4 | CH$_3$ | H | 2HCl | >250° dec. |
| 5 | CH$_3$ | H | HCl | 217-20° |

EXAMPLE 6

The mixture of 315 mg of 1-[2-(2-imidazolylmethyl)phenylthiocarbamoyl]-4-methylpiperazine, 3.3 ml of dimethylformamide, 276 mg of potassium carbonate, 116 mg of cyanogen bromide and 50 mg of 8-crown-6 ether is stirred at room temperature under nitrogen for 3 hours. It is diluted with ethyl acetate, washed with saturated aqueous sodium chloride, dried and evaporated. The residue is dissolved in acetone, the solution treated with 116 mg of maleic acid and diluted with diethyl ether, to yield 5-(4-methyl-1-piperazinyl)-11H-imidazo[1,2-c][1,3]benzodiazepine monomaleate of example 1.

The starting material is prepared as follows:

The mixture of 2.1 g of 11H-imidazo[1,2-c][1,3]benzodiazepine-5(6H)-thione, 23 ml of methylene chloride and 1.0 g of 1-methylpiperazine is stirred at room temperature for 15 hours. The crystalline product formed is filtered off and washed with methylene chloride, to yield 1-[2-(2-imidazolylmethyl)phenylthiocarbamoyl]-4-methylpiperazine.

EXAMPLE 7

A mixture of 9.5 g of 5-methylthio-11H-imidazo[1,2-c][1,3]benzodiazepine hydrochloride, 3.62 g of piperazine, and 350 ml of amyl alcohol is refluxed with stirring and under nitrogen for 20 hours. The solvent is evaporated under vacuum, the residue is triturated with methylene chloride, washed with 2N sodium hydroxide solution, dried over MgSO$_4$, and evaporated to dryness. The residue is dissolved in 10 ml of methanol and treated with 2N ethereal hydrochloric acid solution to give 5-(4H-1-piperazinyl)-11H-imidazo[1,2-c][1,3]benzodiazepine dihydrochloride.

EXAMPLE 8

To a solution of 0.2 g of 5-(4-carboethoxy-1-piperazinyl-11H-imidazo[1,2-c][1,3]benzodiazepine in 2 ml of dry tetrahydrofuran, 100 mg of lithium aluminum hydride are added at once and the mixture is refluxed under nitrogen for 48 hours. The mixture is cooled to room temperature, stirred with 0.2 ml of 30% sodium hydroxide, and filtered. The filtrates are evaporated to dryness and the product is purified to give 5-(4-methyl-1-piperazinyl)-11H-imidazo[1,2-c][1,3]benzodiazepine.

EXAMPLE 9

To a solution of 82 mg of 5-(4-methyl-1-piperazinyl)-11H-imidazo[1,2-c][1,3]benzodiazepine in 1 ml of methylene chloride, 74 mg of m-chloroperbenzoic acid are added at 0°. The mixture is stirred at 0° overnight; this is diluted with 1 ml of ether, one equivalent of ethereal hydrochloric acid solution is added and the resulting precipitate is collected. Recrystallization gives 5-(4-methyl-4-oxido-1-piperazinyl-11H-imidazo[1,2-c][1,3]benzodiazepine hydrochloride.

EXAMPLE 10

To a solution of 100 mg of 5-(4-benzyloxycarbonyl-1-piperazinyl)-11H-imidazo[1,2-c][1,3]benzodiazepine in 0.3 ml of acetic acid are added 0.35 ml of a 2N solution of hydrobromic acid in acetic acid. The mixture is heated at 100° for 1 hour and stirred at room temperature overnight. Ether is added, and the 5-(4H-1-piperazinyl)-11H-imidazo[1,2-c][1,3]benzodiazepine hydrobromide precipitates.

The starting material is prepared similarly to starting material of example 4 by replacing 1-ethoxycarbonylpiperazine with the equivalent amount of 1-benzyloxycarbonylpiperazine.

EXAMPLE 11

A mixture of 265 mg of 5-(4H-1-piperazinyl)-11H-imidazo[1,2-c][1,3]benzodiazepine 0.5 g of potassium carbonate, 0.142 g of methyl iodide and 2 ml of acetone is stirred at room temperature overnight and evaporated. Water is added to the residue, and the mixture is extracted with methylene chloride. The extracts are dried over magnesium sulfate, evaporated, and the residue is purified to give 5-(4-methyl-1-piperazinyl)-11H-imidazo[1,2-c][1,3]benzodiazepine.

EXAMPLE 12

The following compounds of formula I ($R_5$–$R_7$=H) are prepared according to the methods illustrated by the previous examples and are obtained from equivalent amounts of the corresponding substituted starting materials.

| No. | $R_1$ | $R_2$ | $R_3$ | $R_4$ | $C_nH_{2n}$ |
|---|---|---|---|---|---|
| 1 | $CH_3$ | H | $CH_3$ | H | $(CH_2)_2$ |
| 2 | $CH_3$ | $CH_3$ | $CH_3$ | H | $(CH_2)_2$ |
| 3 | H | H | $CH_3$ | 8-$CF_3$ | $(CH_2)_2$ |
| 4 | H | H | $CH_3$ | 8-F | $(CH_2)_2$ |
| 5 | H | H | $CH_3$ | 8-$OCH_3$ | $(CH_2)_2$ |
| 6 | H | H | $CH_3$ | 8-OH | $(CH_2)_2$ |
| 7 | H | H | $CH_3OCH_2CH_2$ | H | $(CH_2)_2$ |
| 8 | H | H | $CH_3COOCH_2CH_2$ | H | $(CH_2)_2$ |
| 9 | H | H | $CH_3$ | 8-$CH_3$ | $(CH_2)_2$ |

EXAMPLE 13

Preparation of 10,000 tablets each containing 25 mg of the active ingredient:

Formula

| | |
|---|---|
| 5-(4-methyl-1-piperazinyl)-11H—imidazo[1,2-c]-[1,3]benzodiazepine | 250.00 g |
| Lactose | 957.00 g |
| Corn Starch | 75.00 g |
| Polyethylene glycol 6,000 | 75.00 g |
| Talcum powder | 75.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 14

Preparation of 10,000 capsules each containing 50 mg of the active ingredient:

Formula

| | |
|---|---|
| 5-(4-methyl-1-piperazinyl)-11H—imidazo[1,2-c][1,3]-benzodiazepine monomaleate | 500.0 g |
| Lactose | 1,400.0 g |
| Talcum powder | 100.0 g |

Procedure

All the powders are passed through a screen with openings of 0.6 mm. Then the drug substance is placed in a suitable mixer and mixed first with the talcum, then with the lactose until homogenous. No. 34 capsules are filled with 200 mg, using a capsule filling machine.

Analogously tablets or capsules are prepared from the remaining compounds of the invention, e.g. those illustrated by the other examples herein.

What is claimed is:

1. The process for the preparation of a compound of the formula

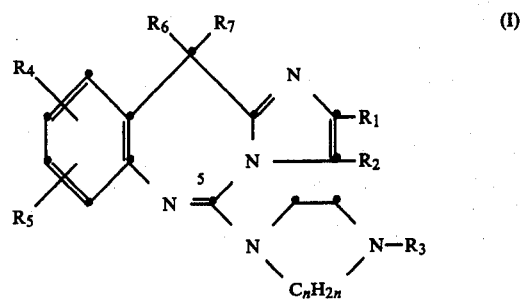

(I)

wherein each of $R_1$ and $R_2$ are hydrogen, lower alkyl, cyano, carboxy, lower alkoxycarbonyl or carbamoyl; $C_nH_{2n}$ is lower alkylene separating both nitrogen atoms by 2 or 3 carbon atoms and n represents the integer 2 to 4: $R_3$ is hydrogen, lower alkyl, lower alkoxycarbonyl or hydroxy-lower alkyl of 2 to 4 carbon atoms; $R_4$ represents hydrogen, lower alkyl, lower alkoxy, lower alkylthio, halogen or trifluoromethyl; $R_5$ represents hydrogen; and $R_6$ and $R_7$ represent hydrogen or lower alkyl; or a pharmaceutically acceptable salt thereof, comprising:

(a) cyclizing a compound of the formula

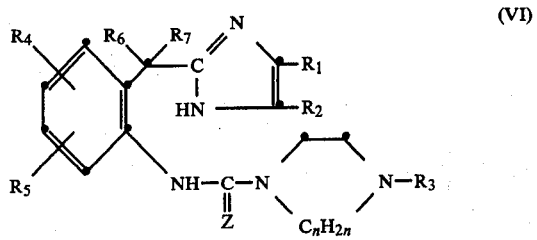

(VI)

wherein Z is oxygen, sulfur, or NH, and the other symbols have the meaning as defined above under dehydrating, dehydrosulfurating or deamination conditions; and if desired (b) converting any resulting compound into another compound of formula I.

2. The process of claim 1 for the preparation of 5-(4-methyl-1-piperazinyl)-11H-imidazo[1,2-c][1,3]benzodiazepine or a pharmaceutically acceptable salt thereof.

3. The process of claim 1 for the preparation of a compound of the formula

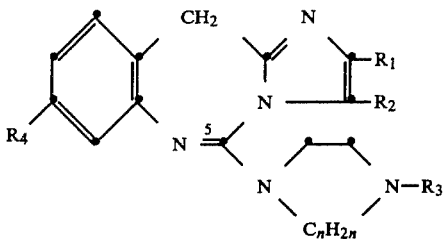

wherein $R_1$ and $R_2$ independently represent hydrogen or lower alkyl; $R_3$ represents hydrogen, lower alkyl or hydroxy-lower alkyl wherein the hydroxy group is separated from the nitrogen atom by 2 carbon atoms; $R_4$ represents hydrogen, lower alkyl, halogen or trifluoromethyl; and $C_nH_{2n}$ represents ethylene or propylene; or a pharmaceutically acceptable salt thereof.

4. The process of claim 3 wherein $C_nH_{2n}$ represents ethylene.

* * * * *